United States Patent [19]

Bukowiecki et al.

[11] Patent Number: 4,567,475
[45] Date of Patent: Jan. 28, 1986

[54] GAS OR VAPOR ALARM SYSTEM INCLUDING SCANNING GAS SENSORS

[75] Inventors: Stanislaw Bukowiecki, Uerikon; Gustav Pfister, Uetikon; Alfons Reis, Stäfa; Alan P. Troup, Männedorf; Hans-Peter Ulli, Zurich, all of Switzerland

[73] Assignee: Cerberus AG, Männedorf, Switzerland

[21] Appl. No.: 481,375

[22] Filed: Apr. 1, 1983

[30] Foreign Application Priority Data

Apr. 15, 1982 [CH] Switzerland ............. 2290/82

[51] Int. Cl.⁴ .............................. G08B 17/10
[52] U.S. Cl. ........................ 340/634; 73/23; 422/98
[58] Field of Search ............ 340/632, 633, 634; 73/23, 27 R; 422/98; 324/71.5; 338/34

[56] References Cited

U.S. PATENT DOCUMENTS

| | | | |
|---|---|---|---|
| 2,583,930 | 1/1952 | Cotton | 340/633 X |
| 3,906,473 | 9/1975 | Levine | 340/634 |
| 3,932,807 | 1/1976 | Wilson | 340/634 X |
| 4,088,986 | 5/1978 | Boucher | 340/628 X |
| 4,160,163 | 7/1979 | Nakauchi | 250/339 |
| 4,399,684 | 8/1983 | Advani et al. | 73/23 X |

FOREIGN PATENT DOCUMENTS

| | | |
|---|---|---|
| 2313413 | 3/1978 | Fed. Rep. of Germany . |
| 2809873 | 9/1978 | Fed. Rep. of Germany . |
| 2383440 | 3/1977 | France . |

OTHER PUBLICATIONS

The Radio and Electronic Engineer, vol. 44, No. 2, Feb. 1974; "Applications of the Tauguchi Gas Sensor to Alarms for Inflammable Gases" by Watson et al., pp. 85–91.

Primary Examiner—James L. Rowland
Assistant Examiner—Daniel Myer
Attorney, Agent, or Firm—Werner W. Kleeman

[57] ABSTRACT

A sensor element responding to gases and/or vapors is heated in at least two temperature cycles continuously from a starting temperature value to an upper temperature value in accordance with a predetermined pattern which is optimized for selective gases. The temperature is lowered to the starting temperature value in accordance with the same or a different pattern. During the temperature cycles a signal which depends on the composition of the gas or vapor atmosphere delivered by the sensor element is compared in an electronic evaluation circuit to stored values which are characteristic for the presence of selective components in the gas and/or vapor.

13 Claims, 4 Drawing Figures

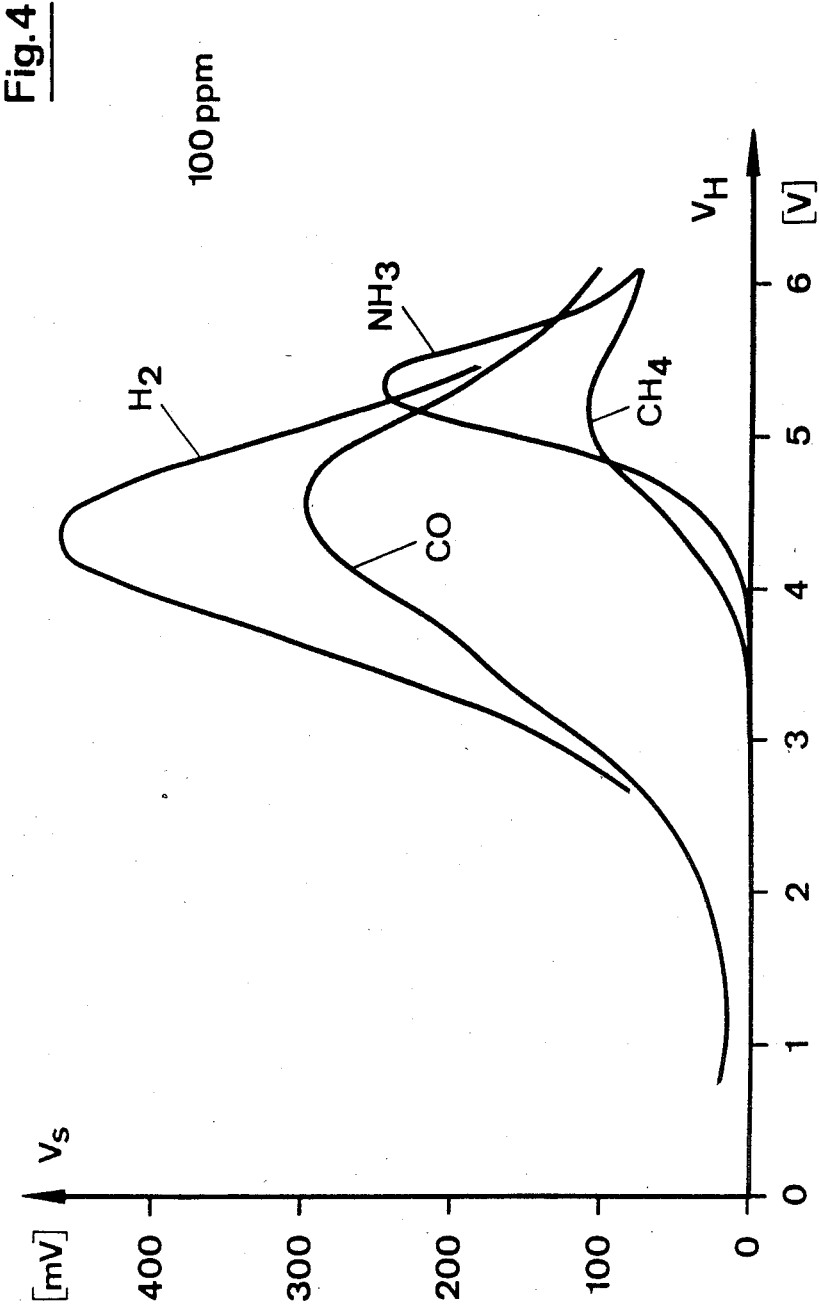

GAS OR VAPOR ALARM SYSTEM INCLUDING SCANNING GAS SENSORS

BACKGROUND OF THE INVENTION

The invention relates to a new and improved gas or vapor alarm system containing at least one heatable and gas-sensitive sensor element and an evaluation or processing circuit.

In present times the environment is endangered and contaminated to a progressively increasing extent, and thus, organic living things or life must be increasingly protected from toxic and explosive gases or chemical vapors. Such protection is of particular importance and urgency in the chemical industry, traffic installations, such as garages or tunnels and in heating installations. Such protection, however, is not feasible without a preceding warning. Metal oxide semiconductors have become fairly well accepted as sensors suitable for such warning purposes. The metal oxide semiconductors (MOS's) react in their heated state, by virtue of a conductivity change thereof, to toxic and/or reducing gases or vapors as well as to water present in their environment. The change in conductivity is utilized as an indication of the integral gas or vapor concentration which is present.

Also, metal oxide beads impregnated with a catalyst have been used for the detection of explosive vapors or gases. The temperature increase, generated by combustion in the environmental air, at the heated surface of the bead is measured and thus serves to establish the presence of combustible gases.

It can be further recognized from research reports that gas sensor elements, like the so-called GAS FETs or CHEMFETs, are being developed on the basis of silicon technology and are supposed to be particularly suited for detecting explosive gases, such as hydrogen, or toxic gases like carbon monoxide, see NTG Fachberichte, Volume 79, 1982.

It has also been mentioned that pyroelectric elements fabricated, for example, of $LiTaO_3$ are sufficiently sensitive to be able to detect temperature variations generated by the desorption of gases from the surface of such sensor element (Chemically Sensitive Devices, Elsevier, 1980).

The sensor elements given here as examples are operated at a constant elevated temperature which is determined by the response time and the cooling time, on the one hand, and by the gas to be measured, on the other hand. While already by virtue of the selection of the value of the constant temperature some preference may be obtained for the detection of individual gases, the sensor elements operated in such manner do not give any information as to the nature of the gas component or the chemical vapor. In such case the sensor element is considered to have a wide or broad band response behavior. For example, certain harmless concentrations of hydrogen produce a change in the electrical conductivity of a metal oxide semiconductor gas sensor element which is of the same magnitude as that which would be produced by a high and dangerous concentration of methane gas. A result thereof is undesirably signalling or indicating a false state-of-danger which frequently entails rather high consequential costs due to, for instance, unnecessary evacuation of an area, production interruption and so forth. There is therefore the desire to selectively detect individual dangerous gases. In practice this requirement has been fulfilled by manufacturing specific gas sensor elements for a certain gas like, for example, a selective sensor element for hydrogen sulphide or for a certain vapor or by equipping a metal-oxide semiconductor with preceding or upstream arranged filters for blocking the access of undesired gases. It is a disadvantage of these techniques that by virtue of such absolute selectivity other components are not detected which are simultaneously present in the environment. Heretofore there thus prevailed the limitation that there was carried out detection of only a single individual gas or vapor component in the environment. Other possibly occurring components were totally neglected. Thus, poisoning phenomena or explosions unfortunately have been known to occur without any response from the alarm system.

In a method for determining the content of a carbon monoxide component in a gas mixture as known, for example, from German Patent Publication No. 2,313,413, published Mar. 2, 1978, a metal-oxide semiconductor is heated to a predetermined temperature by means of a heating wire. After an uncontrolled cooling to room or ambient temperature there is accomplished the carbon monoxide measurement which is differentiated and integrated in a subsequently connected electronic evaluation or processing circuit. The evaluation or processing only occurs in time intervals during which no measurement is accomplished. In this method it is a disadvantage that during the cooling period various gases can settle at the surface of the semiconductor sensor element which then generate a signal similar to that generated by carbon monoxide. Also, at the most only one gas can be selectively detected using this method according to which the gas is detected at constant temperature which is about room temperature. Consequently, as stated hereinbefore, the required degree of selectivity is not ensured.

SUMMARY OF THE INVENTION

Therefore, with the foregoing in mind it is a primary object of the present invention to provide a new and improved gas or vapor alarm system which is not associated with the aforementioned limitations and drawbacks of the prior art systems.

Another and more specific object of the present invention aims at making full use of the wide or broad band sensitivity range particularly of gas sensor elements formed on the basis of metal oxides.

Still a further significant object of the present invention is directed to a new and improved gas or vapor alarm system using sensor elements having a wide or broad band sensitivity range in order to selectively and simultaneously detect individual gases, vapors or types of gases.

Another significant object of the present invention is directed to a new and improved construction of a gas or vapor alarm system comprising one or more gas sensor elements formed, for example, by metal-oxide semiconductors and an electronic evaluation or processing circuit, which alarm system is composed of relatively simple components, is quite economical to manufacture, extremely easy to use, not readily subject to breakdown or malfunction, and affords the high degree of selective sensitivity required in such type of apparatus.

Now in order to implement these and still further objects of the invention, which will become more readily apparent as the description proceeds, the gas or vapor alarm system of the present development is manifested by the features that, the temperature of the sensor is increased in at least two cycles continuously from a starting value to an upper threshold value according to a predetermined pattern which is optimized for individual gases and subsequently decreased to the starting value according to the same or to a different pattern, and the signal indicated by the sensor element during the temperature cycles and depending upon the composition of the gas atmosphere is compared in a subsequently connected electronic circuit with stored values which are characteristic for the presence of predetermined or selective gas and/or vapor components.

BRIEF DESCRIPTION OF THE DRAWINGS

The invention will be better understood and objects other than those set forth above, will become apparent when consideration is given to the following detailed description thereof. Such description makes reference to the annexed drawings wherein:

FIG. 4 is a graphic representation of different output signals obtained for different gases and shows the corresponding response curves.

DETAILED DESCRIPTION OF THE PREFERRED EMBODIMENTS

Describing now the drawings, it is to be understood that only enough of the structure and characteristics of the gas or vapor alarm system according to the invention have been shown as needed for those skilled in the art to readily understand the underlying principles and concepts of the present development, while simplifying the showing of the drawings. Turning attention now specifically to FIG. 1, there is plotted along the abscissa of the depicted graph the heating voltage $V_H$ in volts used for heating-up the metal-oxide semiconductor 1 including the related heating resistor 3 as shown in FIG. 2. The heating voltage $V_H$ produces a temperature lying in the range from room or ambient temperature to 500° C. in the metal-oxide semiconductor 1. By virtue of such temperature range the entire sensitivity range is covered. Along the ordinate of the graph depicted in FIG. 1 the voltage signals $V_S$ are indicated in mV and which are generated as output signals by the metal-oxide semiconductor 1. These signals are proportional to the electrical conductivity of the metal-oxide semiconductor sensor element which changes under the action of the gases or vapors present in its environment and in correspondence with the temperature state thereof. The signals are evaluated or processed in the electronic circuit shown in the block circuit diagram of FIG. 2. In a similar way temperature changes due to the gas atmosphere can be evaluated in the case of a sensor element which detects heat of combustion instead of a change in the electrical conductance or conductivity. The evaluation process will be discussed hereinafter with reference to FIG. 2.

Figure 1:
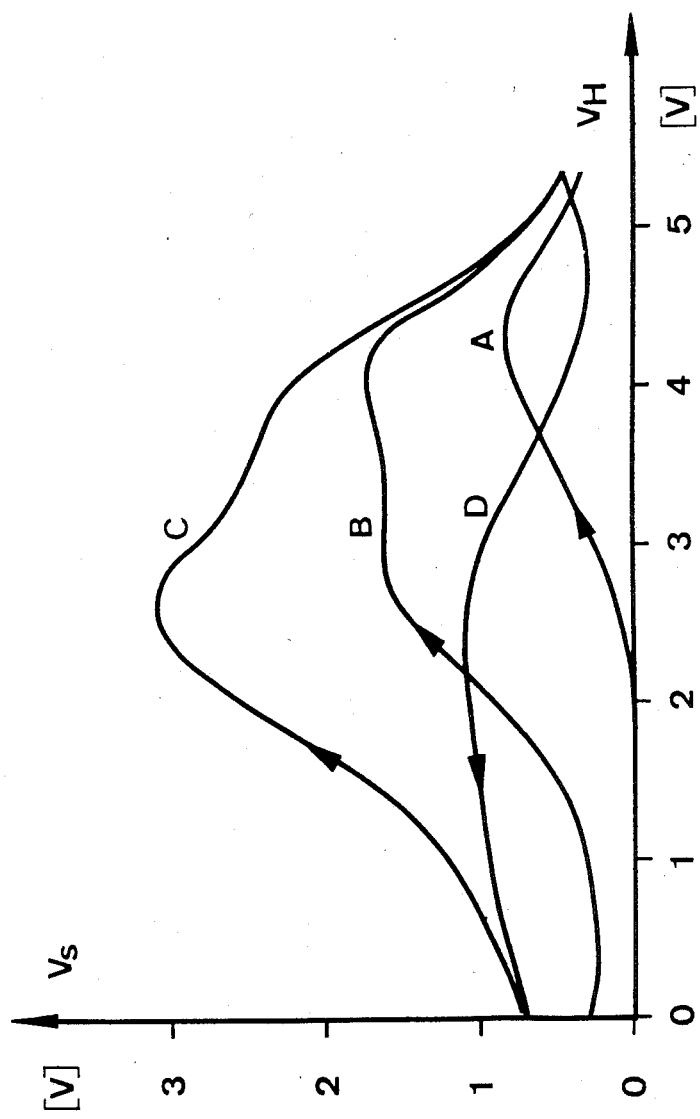
FIG. 1 is a graphic representation of the change in the electric properties of a metal-oxide semiconductor used as a sensor element in a gas or vapor alarm system according to the invention under the action of selective temperature cycles in the presence of different gases and vapors.
Figure 2:
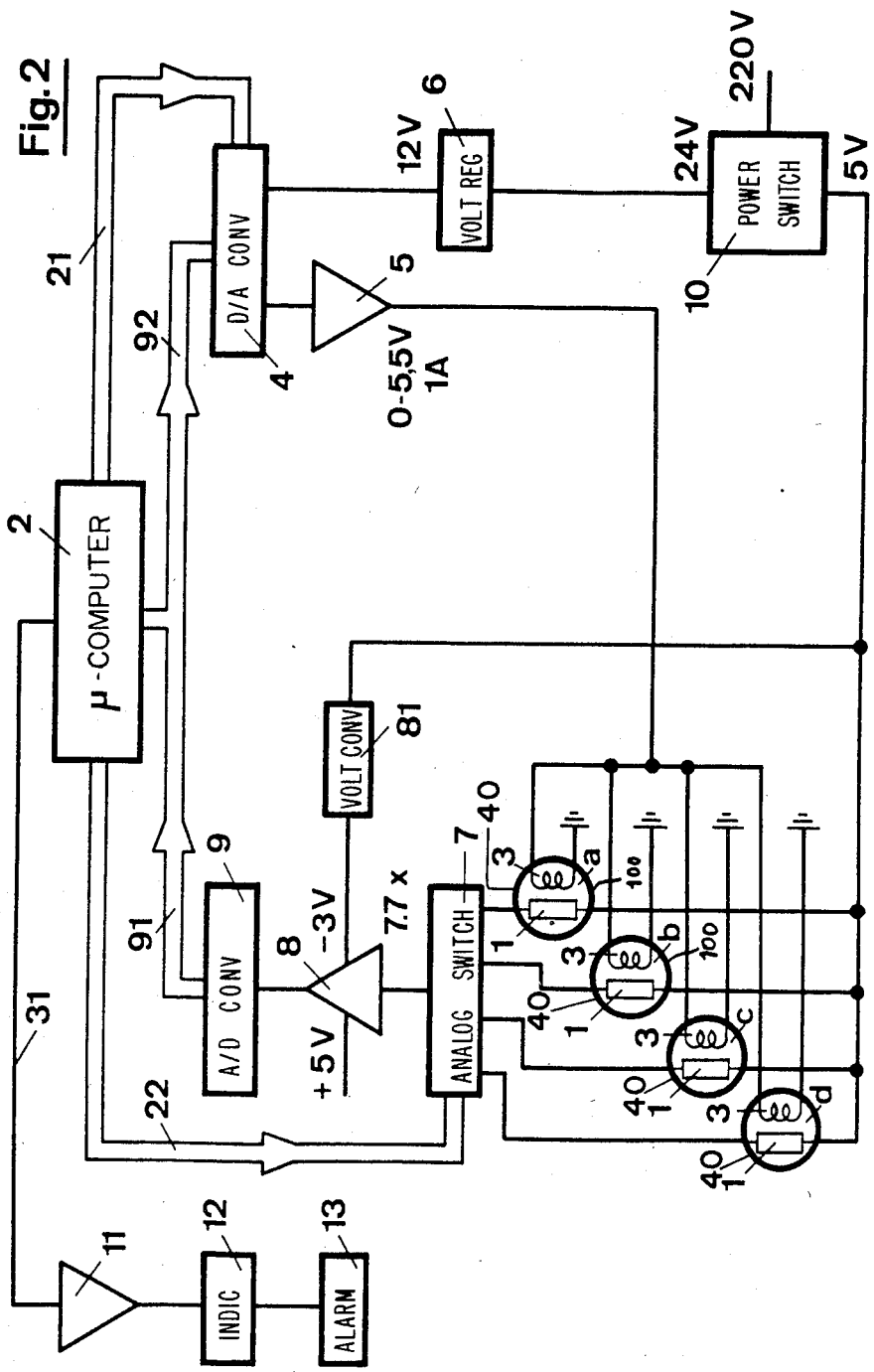
FIG. 2 is a block diagram of the electronic circuit in the gas or vapor alarm system according to the invention for controlling the heating of the metal-oxide semiconductor and for evaluation or processing the output signals thereof which indicate the electric properties of the metal-oxide semiconductor.
Figure 3:
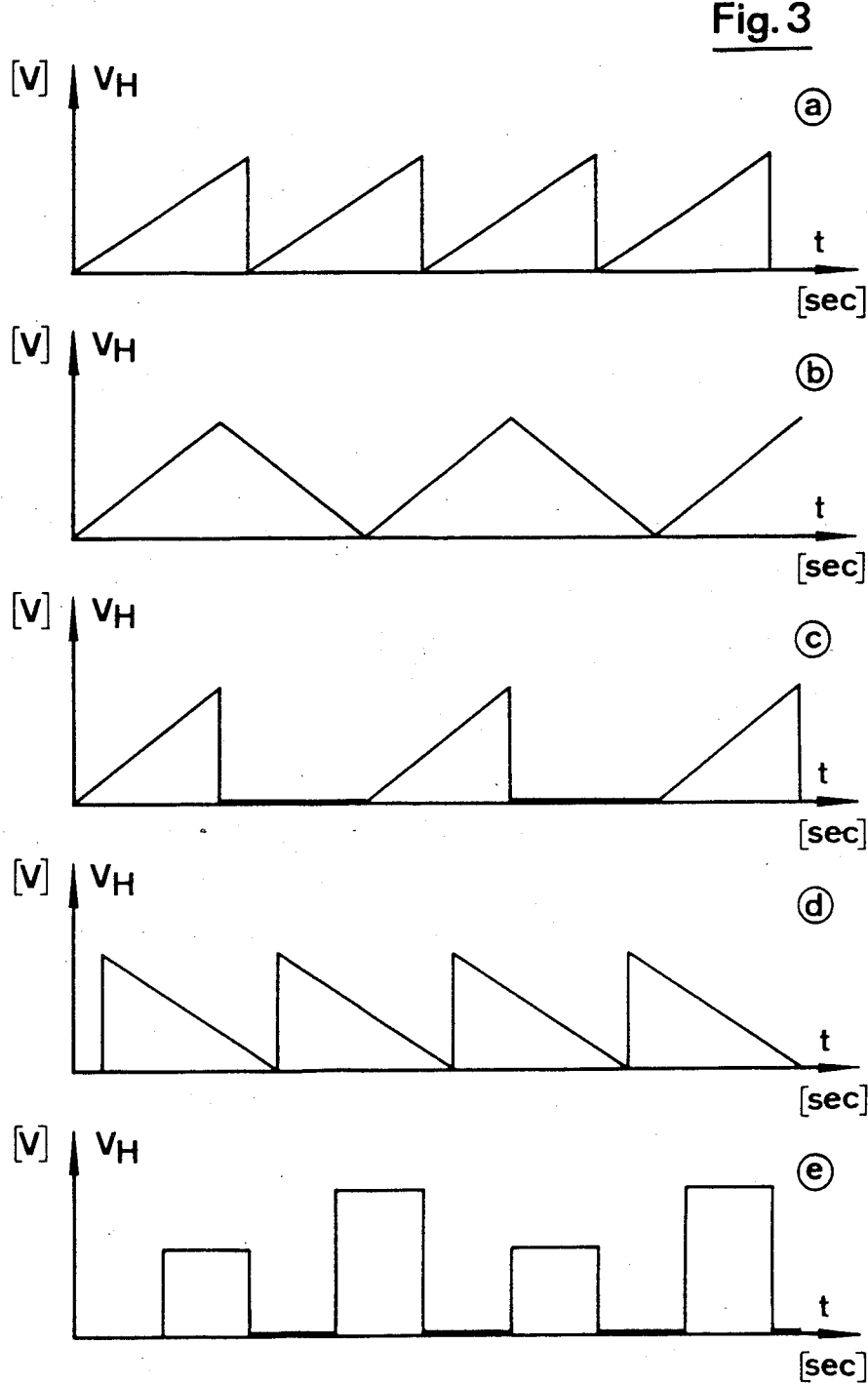
FIGS. 3a to 3e show different patterns of the changes in the heating, voltage during a number of heating and cooling cycles of the metal-oxide semiconductor.

The curve A in FIG. 1 relates to standard air. The increase in the output signal at a heating voltage $V_H$ in the range of 4–5 volts depends upon the air humidity, and thus, can be processed to determine the air humidity. The temperature cycle of the metal-oxide semiconductor, as controlled by the heating voltage, undergoes an excursion to the upper threshold value and then back to the starting value of 0 volts. A temperature cycle having a cycle time of 60 seconds and of FIG. 1 indicated in FIG. 3a was used for recording the curve A. The curves B, C and D indicate the presence of carbon monoxide in an amount of 400 ppm in the environmental or ambient air. The different shapes or envelopes of the curves result from different patterns of the temperature cycles. Thus, there will be evident the eminent significance of the temperature cycle during heating and cooling of the metal-oxide semiconductor. It has been found that by appropriately selecting the temperature cycle the response characteristic can be optimized for individual gases. This will be particularly evident upon comparing the curve C in FIG. 1 to the curve B. The peak value in the curve C is substantially more distinctly expressed or accentuated than in the curve B, although both curves indicate the same concentration of carbon monoxide, namely 400 ppm in the air. The curve B has been generated using the same temperature cycle as shown in FIG. 3a and which was used for recording the background as represented by curve A. The curve C generated using a temperature cycle whose heating voltage follows the path or pattern shown in FIG. 3b. 60 seconds were selected for each of the ascending and descending branches of the heating cycle. The curve D was generated using a heating voltage following the path or pattern shown in FIG. 3d with a cycle time of 60 seconds.

The shape or configuration of the curves shown in FIG. 1 furthermore depend very strongly upon the cycle times for the ascending and descending heating voltage slopes or ramps. The cycle time, in turn, is determined by the geometric structure and properties of the sensor element. For the sensors used in the embodiment discussed herein a cycle time of 60 seconds appeared to be optimal. When using miniaturized sensor elements which have an improved thermal coupling between the heating resistor 3 and the sensor element or material it is then possible to employ more rapid cycle times.

FIG. 2 shows a block circuit diagram of an exemplary embodiment of electronic circuit which can be used for operating, for example, four sensor elements a, b, c and d. It is to be expressly understood, however, that any desired number of sensor elements a, b, c, d can be readily used. The sensor elements or sensors a, b, c, d may either be arranged at different places in one room or area or in different rooms or areas. The sensor elements a, b, c, d may be constituted by metal-oxide semiconductors in the presence or in the absence of catalysts, by beads of ceramic metal oxides preferably containing at least one catalyst, where there is used the effect of generated heat, by MOS-transistors, MIS-diodes or by pyroelectric elements containing a gas absorbing layer.

The metal-oxide semiconductors which form the sensor elements a, b, c, d in the embodiment shown in FIG. 2, for example, may be made of tin dioxide including catalyst additives like, for example, platinum or palladium. Each sensor element a, b, c, d may be considered to comprise a respective heating resistor 3 and one of the metal-oxide semiconductors, generally indicated by reference character 100, or a ceramic metal-oxide represented as a resistor 1 in the drawing. Each one of the resistors 1 is connected to a temperature measuring device 40. A microcomputer 2 constitutes an electronic circuit which controls the heating power or output at each of the sensor elements a, b, c, d via a data bus 21, a digital-to-analog converter 4 and an amplifier 5. The heating voltage $V_H$ is varied according to a pattern or course as programmed in the microcomputer 2. Examples of such patterns have been shown in FIGS. 3a to 3e.

In the embodiment shown in FIG. 2 all four of the sensor elements a, b, c, d are supplied with the same heating power according to the same temperature pattern or course. It will be understood that each heating resistor or resistance 3 of the four sensors a, b, c, d may be individually connected to an amplifier, like the amplifier 5, so that each sensor element or sensor a, b, c, d may have applied thereto an individual temperature pattern programmed by the microcomputer 2. The digital-to-analog converter 4 is powered with current by the voltage regulator 6 which is connected to a suitable power supply 10. The power supply 10 may be, for example, a transformer transforming the standard mains voltage of, for example, 220 volts to the required voltage of, for instance, 24 volts. The sensor elements or sensors a, b, c, d are exposed to environmental or ambient air. During the entire temperature cycle the electrical conductance or conductivity of each sensor element or sensor a, b, c, d is determined by continuously measuring their electrical resistance. In the case of the preferably catalyst-containing ceramic metal-oxides represented by the resistors 1, the temperature measuring devices 40 render an output signal indicative of the temperature of each sensor element or sensor a, b, c, d.

The output signals generated by the sensor elements a, b, c, d are sequentially sampled or scanned by an analog switch 7 and are furnished to the microcomputer 2 via an amplifier 8, an analog-to-digital converter 9 and a data bus 91. The sampling or scanning operation is controlled by the microcomputer 2 via the data bus 22. The output signals of the sensor elements a, b, c, d are processed in the microcomputer 2 in such a way that curves are obtained as shown, for example, in FIG. 1. The measured curves are compared to preprogrammed response cycle patterns which are stored in the microcomputer 2. During such comparison also the temperature cycle is taken into account which results from heating the corresponding sensor element or sensor a, b, c, d. In the event that the comparison results in ambiguities, then the microcomputer 2 will activate the heating resistors 3 via the data bus 21, the digital-to-analog converter 4 and the amplifier 5 in such a manner that a different temperature cycle is obtained. This operation is repeated until the comparison operation performed in the microcomputer 2 renders an unambiguous result. Such result is then, for example, supplied to the amplifier 11 by means of a line 11 and then to a suitable indicating device or printer 12, as the case may be. There the detected gas or the vapors are indicated and dangerous concentrations thereof rendered discernible by the alarm giving or sounding stage 13. In the embodiment shown in FIG. 2 a measuring voltage of 5 volts is indicated at the power supply 10 for generating the output signals of the sensor elements a, b, c, d. This voltage, of course, also can be increased. Such voltage increase will augment or enhance the selective detection gas or of the vapors. A change in such measuring voltage for the sensor elements or sensors a, b, c, d will have to be stored in the microcomputer 2 which, then, will have to take such into account during the various comparison operations. A voltage converter 81 supplies the voltage of $-3$ volts required for operating the amplifier 8.

As already mentioned, FIGS. 3a to 3e show examples of various patterns of temperature cycles.

FIG. 3a shows a continuous increase or ascent of the heating voltage $V_H$ to 5 volts. Thereafter the heating voltage is reduced to 0 volts. The temperature of the sensor element or sensor a, b, c, d changes depending upon the heating voltage. This is a function of the thermal coupling between the heating resistor or resistance 3 and the material of the sensor element or sensor a, b, c, d. The time is plotted in FIG. 3a along the abscissa in seconds. As also already mentioned with reference to FIG. 1, the time for the increase and for the decrease of the heating voltage in each case is 60 seconds. According to FIG. 3a, the heating voltage is again immediately thereafter increased to the same maximum value of 5 volts. Thereafter, the heating voltage drops again to 0 volts. The sensor element or sensor a, b, c, d is heated-up and cooled in a number of temperature cycles. As already mentioned with reference to FIG. 2 the temperature cycles are controlled by the microcomputer 2. This microcomputer 2 also may vary the ascending or descending slope of the heating voltage $V_H$. As desired, greater or smaller voltage values as well as times can be employed. The selection of these parameters will depend upon the evaluation of the output signals delivered by the sensor elements a, b, c, d in the evaluation or processing circuit shown in FIG. 2.

FIG. 3b illustrates that the ascending and the descending branch or leg of the heating voltage $V_H$ have equal lengths and also the same slope. In this example, the time for heating-up the heating resistor 3 of the sensor element a, b, c, d and the time for reducing the heating voltage are 60 seconds. The next heating step follows immediately. Also in this case, the microcomputer 2 may induce changes in the voltage values as well as in the shape of the heating and cooling curves and also in the time t.

According to FIG. 3c the heating voltage $V_H$ is switched-on and switched-off similar to the pattern or cyclic course shown in FIG. 3a (60 seconds), however, with the difference that, here, a time interval of, for example, 60 seconds elapses between the turn-off and the next following turn-on of the heating voltage. Also in this case, the microcomputer 2 may induce changes in the voltage values as well as in the shape of the voltage curve and in the time t. This will depend, as already previously mentioned a number of times, in accordance with the evaluation of the output signals furnished by the sensor elements a, b, c, d.

FIG. 3d shows an immediate increase of the heating voltage $V_H$ to the maximum value at the moment the heating is turned on and a slow decrease of the heating voltage. This again occurs within a time span or interval of 60 seconds. Thereafter the heating voltage $V_H$ is again switched to the maximum value of, for example, 4 volts and again slowly decreased. Also, in this example, the microcomputer 2 may induce changes depending upon the evaluation of the output signals from the sensor element or sensor a, b, c, d as, for example, in the voltage values, in the shape of the heating or cooling curve and in the time t.

FIG. 3e shows an instantaneous increase of the heating voltage to a value of 3 volts. The heating voltage remains constant for a time period of 60 seconds and, then, decreases again. Thereafter the sensor element a, b, c, d is not heated for approximately the same time. The next following heating-up phase occurs in the same pattern but to a higher voltage value, such as for example, 6 volts. With this procedure there is intended to be illustrated that the microcomputer 2 already has changed the voltage value.

Since FIGS. 3a to 3e only illustrate examples it will be understood that the heating voltage also may be increased or decreased in other wave-like shapes and also the time t can be changed.

FIG. 4 shows response curves for the gases hydrogen, carbon monoxide, ammonia and methane which individually have been mixed with air at a volume concentration of 0.01 percent by volume which corresponds to 100 ppm. The profiles or envelopes have been recorded using the temperature cycle indicated in FIG. 3a. The different shapes of the response curves are clearly recognized and they are characteristic for the selective gases. In particular the response maxima are located at different heating voltages. The exact shape of the curves therein depends upon the thermal coupling between the heating resistor 3 and the material of the sensor element a, b, c, d. Also, the shape of the curves is strongly affected by the addition of suitable catalysts.

While there are shown and described present preferred embodiments of the invention, it is to be distinctly understood that the invention is not limited thereto, but may be otherwise variously embodied and practiced within the scope of the following claims.

Accordingly, what we claim is:

1. A gas or vapor alarm system comprising:
at least one heatable sensor element for generating an output signal in dependency upon the presence of a gas or vapor;
heating means for continuously changing the temperature of said sensor element through at least two temperature cycles from a starting value to an upper threshold value in accordance with a predetermined pattern and thereafter back to said starting value according to a preselected pattern, which patterns are optimized with respect to selective ones of said gases or vapors;
said output signal of said sensor element varying during said temperature cycles as a function of the composition of said gas or vapor;
an electronic circuit for receiving the output signals of the sensor element; and
said electronic circuit comparing the variation of said output signal during said temperature cycle of said sensor element with stored ones of such variations which are characteristic for the presence of predetermined components of said gas or vapor.

2. The alarm system as defined in claim 1, wherein:
said sensor element comprises a heatable semiconductor element on the basis of a ceramic metal-oxide;
said semiconductor element having a conductance which changes as a function of the environmental gas atmosphere and thus serves to generate said output signal.

3. The alarm system as defined in claim 2, further including:
at least one catalyst provided for said sensor element optimizing the detection of predetermined ones of said gases or vapors.

4. The alarm system as defined in claim 1, further including:
a temperature measuring device;
a heatable ceramic metal-oxide forming said sensor element;
at least one catalyst provided for said ceramic metal-oxide; and
said ceramic metal-oxide being attached to said temperature measuring device by means of which the temperature increase generated by the interaction of said sensor element with said gas or vapor forms said output signal.

5. The alarm system as defined in claim 1, wherein:
said sensor element comprises a modified heatable semiconductor component having a gas or vapor dependent characteristic and used for generating said output signal.

6. The alarm system as defined in claim 5, wherein:
said semiconductor component comprises a MIS-diode.

7. The alarm system as defined in claim 5, wherein:
said semiconductor component comprises a MOS-transistor.

8. The alarm system as defined in claim 1, wherein:
said sensor element comprises a heatable pyroelectric element provided with a gas or vapor absorbing layer;
said gas or vapor is absorbed at said heatable pyroelectric element during a cooling phase of said temperature cycles; and
a pyroelectric current of said heatable pyroelectric element is modified by desorbing said gas or vapor from said heatable pyroelectric element and utilized as said output signal.

9. The alarm system as defined in claim 1, wherein:
said electronic circuit contains means enabling providing different temperature cycles for individual ones of said sensor elements.

10. The alarm system as defined in claim 1, wherein:
said electronic circuit contains means for varying said temperature cycles in correspondence to said output signal received by said electronic circuit in order to optimize the indication of detected ones of said components in said gas or vapor.

11. The alarm system as defined in claim 1, wherein:
a plurality of said sensor elements are provided;
said temperature cycles have starting times, cycle periods and temperature patterns; and
said starting times, said cycle periods and said temperature patterns are different for individual ones of said plurality of sensor elements.

12. The alarm system as defined in claim 1, wherein:
said heating means continuously change the temperature of said sensor element through at least two temperature cycles from a starting value to an upper threshold value in accordance with said predetermined pattern and thereafter back to said starting value according to said preselected pattern which corresponds to said predetermined pattern.

13. The alarm system as defined in claim 1, wherein:
said heating means continuously change the temperature of said sensor element through at least two temperature cycles from a starting value to an upper threshold value in accordance with said predetermined pattern and thereafter back to said starting value according to said preselected pattern which is different from and does not correspond to said predetermined pattern.

* * * * *